United States Patent [19]

Mc Partland et al.

[11] 4,117,834

[45] Oct. 3, 1978

[54] PHYSIOLOGICAL MOTOR ACTIVITY MONITORING APPARATUS

[76] Inventors: Richard J. Mc Partland, 5995 Library Rd., Bethel Park, Pa. 15102; F. Gordon Foster, 6409 Howe St., Pittsburgh, Pa. 15206; David J. Kupfer, 834 Amberson Ave., Pittsburgh, Pa. 15232

[21] Appl. No.: 746,852

[22] Filed: Dec. 2, 1976

[51] Int. Cl.$^2$ .............................................. A61B 5/10
[52] U.S. Cl. .................................. 128/2 S; 128/2 N; 35/22 R
[58] Field of Search .......... 128/2 S, 2 N, 2 R, 2.05 P, 128/2.05 T, 2.06 A, 419 PG; 35/22 R; 340/279

[56] References Cited

U.S. PATENT DOCUMENTS

| 3,633,569 | 1/1972 | Brayshaw et al. | 128/2.06 A |
|---|---|---|---|
| 3,756,245 | 9/1973 | Thaler et al. | 128/419 PG X |
| 3,929,335 | 12/1975 | Malick | 340/279 X |

FOREIGN PATENT DOCUMENTS

| 1,383,594 | 2/1975 | United Kingdom | 128/2 S |
| 302,103 | 6/1971 | U.S.S.R. | 128/2 S |

OTHER PUBLICATIONS

Colbum et al., "An Ambulatory Activity Monitor . . . Memory", ISA Transactions, vol. 15, No. 2, pp. 149–154, May 5, 1976.

Arechiga et al., "An Accurate and Simple Method to Analyse Neuronal Activity . . . ", Marine Behavior & Phys., vol. 2, No. 4, pp. 307–310, Aug. 1974.

*Primary Examiner*—Lee S. Cohen
*Attorney, Agent, or Firm*—Buell, Blenko & Ziesenheim

[57] ABSTRACT

A combination of modular devices in capsule form adapted to be worn on the person, as with a watchband or belt, for detecting and accumulating the occurrence of specific physiological events and to alert the wearer upon the occurrence of a predetermined number of such events. One embodiment comprises the combination of a motion detecting transducer, an accumulator incremented for $2^n$ number of movements and a 4-digit light-emitting diode alerting-display module for providing a visual signal that an allowed number of events has occurred. A modified embodiment comprises the combination of a motion detecting transducer, a data accumulator incremented for $2^n$ number of movements in a selected accumulation interval, and a multi-cell random-access-memory to which the contents of the accumulator are transferred and stored at the termination of each accumulation interval delineated by a timer module, i.e., the time intervals of data accumulation are defined by the output pulse of a quartz crystal oscillator and frequency divider.

10 Claims, 2 Drawing Figures

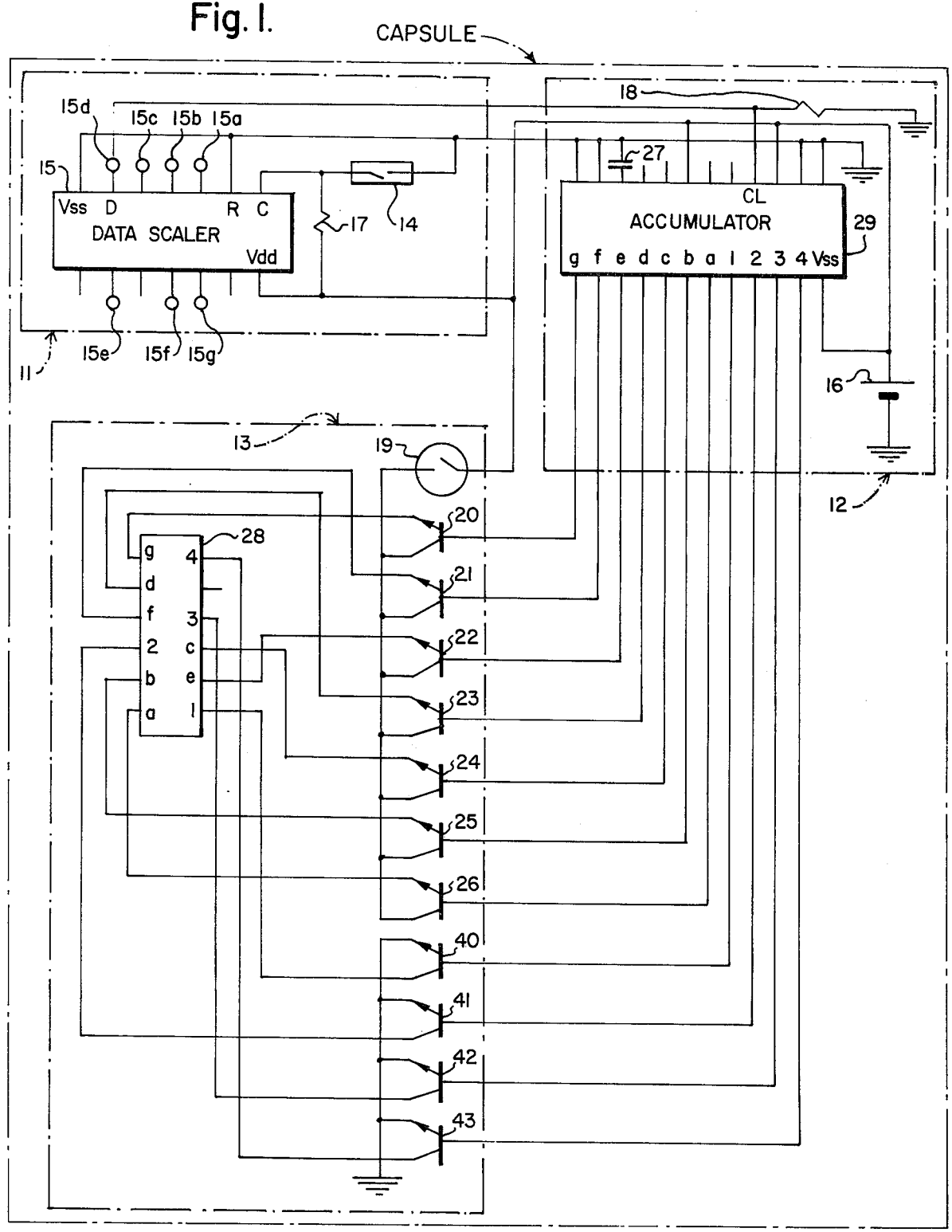

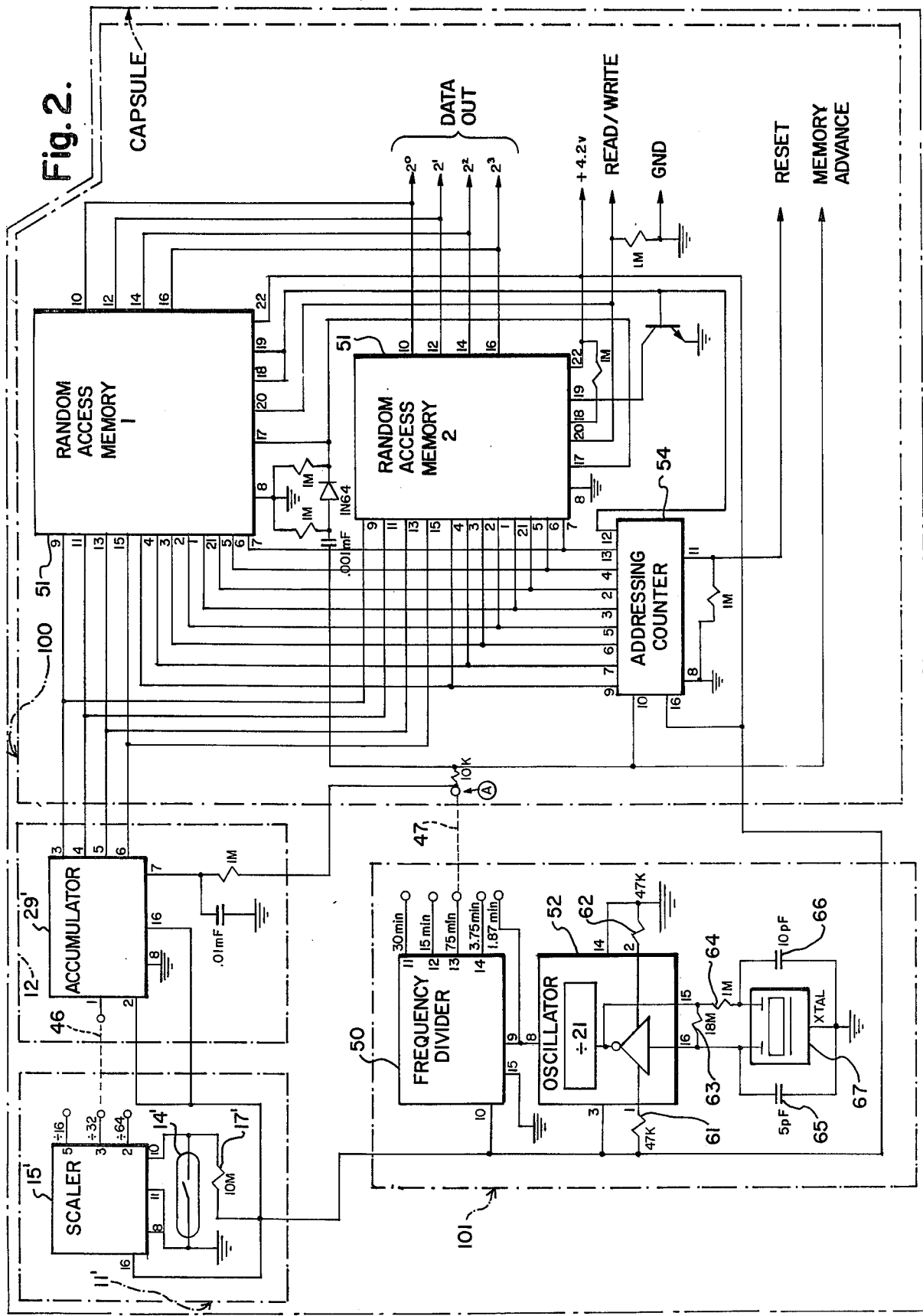

PHYSIOLOGICAL MOTOR ACTIVITY MONITORING APPARATUS

This invention relates to apparatus for monitoring physiological motor activity of human beings or animals, primarily in the medical field, though having uses in other areas such as in efficiency studies for industry or in exercise monitoring for athletics. In the medical field, the apparatus has utility for physicians, as well as for patients, in the management of chronic medical, neurologic, and psychiatric disorders. The apparatus is adapted for quantitatively measuring motor activity in physical and for mental states sometimes necessitating pharmacological management and periodic re-evaluation of the need for medication and proper maintenance drug level.

It is the purpose of our invention to provide apparatus for detecting the accumulating data on the occurrence of physiological motor activity and to alert the user of the apparatus to the occurrence of a predetermined number of such events. More specifically, it is the purpose of our invention to provide apparatus which will alert the user that an allowed or pre-set number of events has transpired and that he should rest, take medication or contact his physician. Thus, a cardiac patient, limited to a specified amount of motor activity per day, may use the apparatus to proportion his activity into 4-hour intervals and by consulting the apparatus at the beginning of each 4-hour interval, warn himself if he exceeds his allowed amount of motor activity.

In attaining the above purposes, we provide in capsule form adapted to be worn on the person as by a watchband or belt, a combination of modular elements comprising (1) physiological event (motion) detector module and (2) an accumulator module.

More specifically, we provide a transducer which functions to detect the physiological event (motor movement) and forwards a series of electronic pulses, (one for each event or multiple of events detected) to the accumulator module.

We further provide, in capsule form, the combination of modules (1) and (2) heretofore mentioned and a further auxiliary modular element (3) the alerting-display module, which serves to alert the user by a visual, auditory or tactile alarm, when a number of events, preselected by the user, have transpired.

We further provide an additional combination of elements having a modified form of accumulator module, by which, upon termination of the data accumulation interval, indicated by the output of a timer module, the data content of the accumulator is transferred to a multi-cell random-access-memory, the accumulator is reset to zero and a new accumulation interval is begun.

A preferred form of our invention is hereinafter further described, in greater detail, in connection with the accompanying drawings, wherein:

FIG. 1 is a diagrammatic illustration of a simpler embodiment of the invention, and FIG. 2 is a diagrammatic illustration of another embodiment of the invention with further refinements and sophistication.

Referring to FIG. 1 of the drawings, the embodiment of the invention there shown diagrammatically comprises a combination of elements, presently to be identified, housed in a capsular casing, of suitable lightweight material such as milled plexiglass plastic or molded epoxy, and an overall size of the order of 3.8 × 4.5 × 2.2 cm and 51 gram weight (including battery). The elements shown include the basic combination of a physiological event detector module (including transducer) 11 an accumulator module 12, and an alerting-display module 13.

Associated with the module 11 is a mercury switch 14, in capsule form, which detects movements of the body causing transverse or rotational movement of the transducer. We prefer a switch having a sensitivity such as to detect all linear movements above a 6 millimeter (mm) displacement threshold and all rotational movements above 8° of arc (measured with a radius of 8 centimeters (cm)).

The module 11 also contains an electronic integrated circuit device 15, in the form of a multiple stage binary counter, obtainable as a standard commercial item (RCA-CD4024AK). It has a number of terminals 15a, 15b, 15c, 15d, 15e, 15f and 15g (shown illustratively as seven in number) for providing a selectable scaling factor variable with the terminal employed. The scaling factor divides the number of movements by 2, 4, 8, 16, 32, 64, or 128 respectively. The device 15 is accordingly identified in the drawing by the legend "DATA SCALER".

The module 11 is connected to an accumulator module 12, preferably through printed circuit board wiring, in circuit with a 4.05 volt DC battery 16 (e.g. Mallory TR-163), and two resistors 17 (10m ohm) and 18 (13K ohm). The output of the module 11 is a series of electronic pulses, one for each event (or multiple thereof dependent on the scale employed) to the input terminal (marked CL) of the counter-latch and decoder integrated circuitry 29 contained in module 12. Integrated circuitry 29 may be a commercially obtainable item, such as Mostek Corp. MK5005P integrated circuit. Also included in module 12 is one capacitor (0.01 mfd) 27.

The alerting-display module 13 is comprised of commercially obtainable items as follows: one multi-digit light-emitting diode visual display 28 (Hewlett Packard 5082-7414), eleven transistors (code 2N2925), 20, 21, 22, 23, 24, 25, 26, 40, 41, 42, and 43 and a display activating switch 19 preferably of the reed type. The light-emitting diode display is activated on closing of the switch 19. The switch 19 is so connected in circuit with the positive voltage supply to module 13 that closing of the switch, effected merely by holding a small bar magnet in contact with the side of the total unit, activates the display 28. Conversely, removal of the magnet causes the switch to open, thereby deactivating display 28. The display 28 of module 13 also serves to alert the user when a preselected number of events have transpired.

The terminals of module 12, identified as 1, 2, 3 and 4, a, b, c, d, e, f and g of integrated circuitry 29 are connected via printed circuit board wiring to correspondingly numbered terminals of display 28. Transistors 40, 41, 42, 43, 26, 25, 24, 23, 22, 21 and 20 are interposed respectively in this wiring.

It will be seen that the apparatus consisting of modules 11, 12, 13 is of great importance for physicians and patients in the control of chronic medical, neurologic and psychiatric disorders. It will be understood also that when used it provides a viable system sufficient to manually record data at specific times or periods throughout the day. It can alert the user that the allowed number of events has transpired and that he should rest, take medication or contact his physician. For example, a cardiac patient is allowed a specific amount of motor activity per day. The patient will proportion his activity into 4-hour intervals and consult the unit at the beginning of each 4-hour interval, to warn himself if he exceeds the allowed amount of motor activity.

Referring to FIG. 2, there is shown another embodiment of physiological monitoring apparatus which utilizes essentially the same type of modules utilized in the first described embodiment, with the addition of multi-cell memory means for automatically storing the maximum count of the accumulator at the termination of repetitive sequential time intervals, and the addition of means for delineating intervals of time, and with the deletion of the alerting display module 13 of FIG. 1.

All of the elements or modules employed in this embodiment are obtainable commercially. Elements in FIG. 2 corresponding in function to those of FIG. 1 are identified by the corresponding reference numeral with the prime (') suffix. Thus modules 11' and 12' are a physiological event (motion) detector module and an accumulator module, respectively. While the timer module 101 and memory module 100 are unique to the unit of FIG. 2, the data scaler 15' may be an integrated circuit item (RCA-CD4040) whereas the accumulator 29' may be combined with a frequency divider 50 as one item (RCA-CD4520). The accumulator is incremented for $2^n$ number of movements (2, 4, 8, 16, 32, 64 or 128). Alternative connections of accumulator 29' to scaler 15' are indicated by the broken line 46 therebetween. Upon termination of the current accumulation interval, the data content of the accumulator are transferred to a cell in the memory module 100, then the accumulator is reset to zero and a new accumulation interval is begun which terminates in a similar manner. Thus the amount of motor activity is monitored and stored for many successive time intervals with the results of each time interval being deposited in one or more unique cells of one or more, illustratively shown as two in number, random access memory integrated circuits 51. The integrated circuits 51 may be commercial items, such as INTEL 5101, each having 256 or more cells.

The time intervals for recording data on the accumulator are delineated by the timer module 101 which is comprised of a quartz crystal oscillator integrated circuit (RCA-CD4045) 52 along with resistors 61, 62, 63 and 64, capacitors 65 and 66, and crystal 67 and of a frequency divider integrated circuit (one half of RCA-CD4520) 50. Each successive time interval is terminated by a timing pulse from the frequency divider. The duration of this time interval depends on the crystal frequency and the number of flip-flop stages used in the frequency divider circuit. Each flip-flop stage divides the frequency by 2. Using an 18.651 KHz crystal, intervals of 1.875, 3.75, 7.5, 15, or 30 minutes can be chosen depending on whether 21, 22, 23, 24 or 25 flip-flop stages are employed. Alternative connections from memory module 100 to timer module 101 are indicated by the broken line 47.

At the termination of each summing interval, marked by a timing pulse from the frequency divider, the data content of the accumulator (i.e., the number of activity units summed during the preceding time interval) are deposited into the memory cells of memory module 100, specifically into cells of one of the integrated circuits 51 and the accumulator 29' is reset to 0.

An addressing counter 54, which may be a commercial item such as RCA-CD4040, controls which cell of the memory circuits 51 receives data. The counter is initially set to 0 and is incremented by 1 after each transfer of data from the accumulator 29' to cells of the memory circuits 51. In this manner, each memory cell is sequentially filled at the rate of one cell for each time interval, and the data content of each memory cell represents the activity unit total for its respective time interval.

As all the ramdom access memory cells become full, data is transferred from the memory cells to an external permanent storage medium via lines indicated by the legend "data out", so that the monitoring apparatus may be reused and the data analyzed.

As in the case of the embodiment of FIG. 1, this embodiment of the apparatus is in a compact capsule housed in a case, such as lucite or epoxy, measuring 4.0 × 2.0 × 2.0 cm including batteries and weighing approximately 35 grams or less.

While we have shown and described herein specific preferred embodiments, it will be apparent that variations or modifications may be made therein within the terms of the appended claims. Circuit interconnects may be by wire, printed circuit, thick film, thin film or other.

We claim:

1. Apparatus for monitoring physiological motor activity comprising a miniaturized capsule adapted to be affixed to and worn by the person being monitored, said capsule containing:
   (a) a motion sensing means sensitive to linear and rotational movements of said capsule,
   (b) electronic scaling means in circuit with said motion sensing means for providing an output of pulses corresponding in number to units of motor activity, each unit of which comprises a predetermined plurality of said movements, as registered by said motion sensing means,
   (c) an integrated electronic accumulator connected to said scaling means for accumulating said output of pulses from said scaling means, and
   (d) an electronic-sensory means for registering and signalling the output of pulses in said accumulator relating to the number of units of motor activity.

2. Apparatus for monitoring physiological motor activity, according to claim 1, wherein said motion sensing means comprises a mercury switch sensitive to linear and rotational movements of the capsule.

3. Apparatus for monitoring physiological motor activity, according to claim 1, wherein said apparatus further comprises:
   (a) a direct current battery having a voltage of approximately 4 volts, and
   (b) printed circuit wiring connecting said battery in circuit with said electronic scaling means, said integrated electronic accumulator and said electronic-sensory means.

4. Apparatus for monitoring physiological motor activity according to claim 1, wherein said electronic scaling means comprises a multiple stage binary counter and said integrated electronic accumulator comprises a counter-latch-decoder integrated circuit.

5. Apparatus for monitoring physiological motor activity according to claim 1, wherein said electronic scaling means comprises means including a series of different terminals to which circuit connections are selectively made for scaling the units of motor activity according to a dividing factor of $2^n$, where n is any number taken from a group of selected integers.

6. Apparatus for monitoring physiological motor activity according to claim 1, wherein said electronic-sensory means comprises a plurality of light-emitting diodes arranged to provide a multi-digit display of the number of units of motor activity.

7. Apparatus for monitoring physiological motor activity according to claim 1, wherein said apparatus further comprises a magnetically operated reed switch in circuit with said electronic-sensory means and said integrated electronic accumulator and adapted to be closed by placement of a magnet in proximity to said capsule to activate said apparatus.

8. Apparatus for monitoring physiological motor activity comprising a miniaturized capsule adapted to be affixed to and worn by the person being monitored, said capsule containing:

(a) a motion sensing means sensitive to linear and rotational movements of said capsule, (b) electronic scaling means in circuit with said motion sensing means for providing an output of pulses corresponding in number to units of motor activity, each unit of which comprises a predetermined plurality of said movements, as registered by said motion sensing means, (c) an integrated electronic accumulator connected to said scaling means for accumulating said output of pulses from said scaling means, (d) multi-cell random-access-memory means connected to said accumulator, and (e) a quartz crystal oscillator and a frequency divider means cooperatively functioning to provide timing pulses at timed intervals to said accumulator whereby to effect the delivery repetitively by said accumulator of the output of pulses relating to the number of units of activity accumulated thereon during the immediately preceding timed interval to said memory means.

9. Apparatus for monitoring physiological motor activity, according to claim 8, wherein said apparatus further comprises electronic addressing counter means for directing the data as to number of units of activity to successive cells of said memory means.

10. Apparatus for monitoring physiological motor activity, according to claim 9, wherein said apparatus additionally comprises means for transferring data from said memory means to an external permanent storage means.

* * * * *

Disclaimer 4,117,834.—*Richard J. McPartland; F. Gordon Foster* and *David J. Kupfer*, Pittsburgh, Pa. PHYSIOLOGICAL MOTOR ACTIVITY MONITORING APPARATUS. Patent dated Oct. 3, 1978. Disclaimer filed Feb. 5, 1982, by the inventors.

Hereby enters this disclaimer to claims 8, 9 and 10 of said patent.

[*Official Gazette May 4, 1982.*]